United States Patent [19]

Maruyama et al.

[11] 4,053,382

[45] Oct. 11, 1977

[54] LIQUID JUNCTION OF REFERENCE ELECTRODE

[75] Inventors: Hiroshi Maruyama; Masashi Watanabe, both of Kyoto, Japan

[73] Assignee: Horiba, Ltd., Japan

[21] Appl. No.: 655,975

[22] Filed: Feb. 6, 1976

[30] Foreign Application Priority Data

Feb. 25, 1975 Japan .................................. 50-23621

[51] Int. Cl.² .......................................... G01N 27/30
[52] U.S. Cl. ................................................ 204/195 F
[58] Field of Search ............... 204/195 F, 195 P, 1 H, 204/1 A, 195 M; 324/30 R

[56] References Cited

U.S. PATENT DOCUMENTS

| 3,498,899 | 3/1970 | Kater et al. ..................... 204/195 F |
| 3,856,649 | 12/1974 | Genshaw et al. ................ 204/195 F |

FOREIGN PATENT DOCUMENTS 878,722  8/1971  Canada ............................. 204/195 F Primary Examiner—G. L. Kaplan
Attorney, Agent, or Firm—Wenderoth, Lind & Ponack

[57] ABSTRACT

An improved liquid junction for a reference electrode is provided. It is characterized by forming a hydrophilic layer by treatment of only the surface of a liquid junction of a polymer of tetrafluoroethylene.

5 Claims, 6 Drawing Figures

LIQUID JUNCTION OF REFERENCE ELECTRODE

BRIEF DESCRIPTION OF THE INVENTION

The present invention relates to an improved liquid junction for a reference electrode used in the measurement of ionic concentration of a solution.

BRIEF DESCRIPTION OF THE DRAWINGS

The attached drawings depict several embodiments of the electrodes employing the liquid junctions of the present invention.

BACKGROUND OF THE INVENTION

The measurement of ionic concentration of a solution, such as the measurement of pH value by electrode potential, is generally performed by immersing a glass electrode and a reference electrode in the solution, wherein desired conditions are 1. the liquid-liquid potential difference between the liquid junction and the solution is as small as possible and at the same time 2. the leak of an internal liquid of the liquid junction is also as negligible as possible.

It is generally true that although liquid junctions prepared from well-known polytetrafluoroethylene or other hydrophobic plastic materials have the advantage of low leakage due to their hydrophobic or water-repulsive properties, they also have the disadvantage of a large potential difference at the boundary surface between the liquid junction and the solution to be measured. In order to overcome such disadvantage, the following measure has been previously employed.

An electrolyte such as potassium chloride, etc. in a solid state or in a solution state is mixed with polytetrafluoroethylene or other hydrophobic plastic materials or these plastic materials are impregnated with the electrolyte forcibly, and moreover, if necessary, these materials are mixed with a glass powder, etc. to increase the hydrophilicity.

By this measure, it is possible to decrease the liquid-liquid potential difference at the boundary surface between the liquid junction and the solution. However, on the other hand, disadvantageously large leaks cannot be avoided since the liquid junction in this case is completely composed of a modified plastic material having hydrophilic properties which lacks its original hydrophobic or water-repulsive properties which are useful for minimizing internal leaks of the liquid of the liquid junction.

The present invention has as its objective to overcome the disadvantages of the conventional liquid junctions mentioned above and to provide a liquid junction which satisfies the said both conditions; i.e. a small liquid-liquid potential difference and the negligible leakage of the internal liquid of the liquid junction.

DETAILED DESCRIPTION OF THE INVENTION

In the following, the invention will be explained in detail with reference to several drawings of embodiments of the invention.

Figure 1:
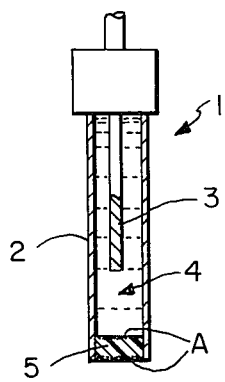
FIGS. 1 and 2 are vertical sections of a first embodiment.
Figure 2:
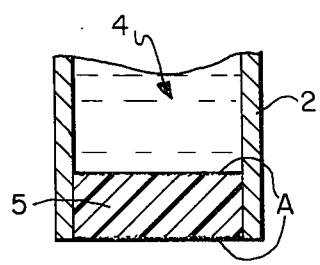

In FIG. 1 and FIG. 2, 1 is a reference electrode used, for example, for the determination of the pH value of a solution, 2 is a supporter tube for the reference electrode, 3 is an internal electrode such as a silver chloride electrode or calomel electrode, 4 is an internal liquid such as saturated potassium chloride solution, etc. and 5 is the liquid junction of the present invention consisting of the hydrophobic plastic Teflon (polymer of tetrafluoroethylene), wherein only on the surface area of the liquid junction, a hydrophilic layer A is formed. The formation of the hydrophilic layer A can be understood from the following, where Teflon is used as the material. If the surface of liquid junction consisting of Teflon is treated with metallic sodium, C-F linkages in Teflon molecules whose chemical structure is

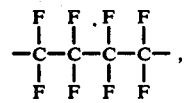

break down at the surface of the liquid junction and form a layer mainly consisting of a carbon skeleton at the surface. Here, the hydrophilic layer A is formed, since the layer only consisting of carbon skeleton has a hydrophilic property.

A practical embodiment of the said surface treatment is to immerse the material for liquid junction consisting of Teflon in an organic solvent mainly comprising naphthalene and containing metallic sodium.

Figure 3:
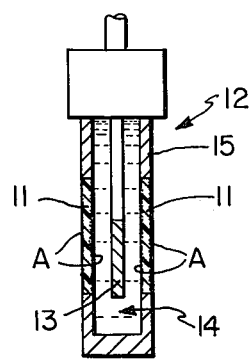
FIG. 3 is a vertical section of a second embodiment.

FIG. 3 depicts a second embodiment of the present invention, wherein a liquid junction 11 is provided around the side wall of a reference electrode 12 and not at the bottom of it. In this Figure, 13 is an internal electrode, 14 is an internal liquid and 15 is a supporter tube.

Figure 4:
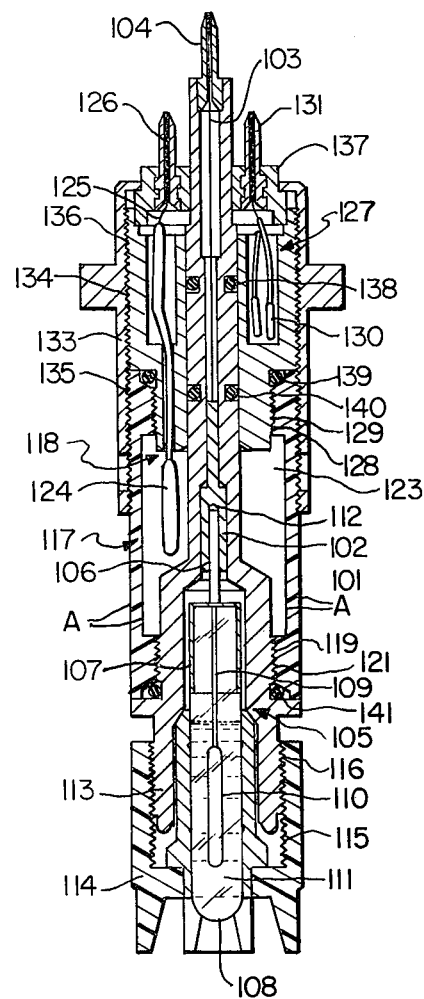
FIG. 4 is a vertical section of the third embodiment.
Figure 5:
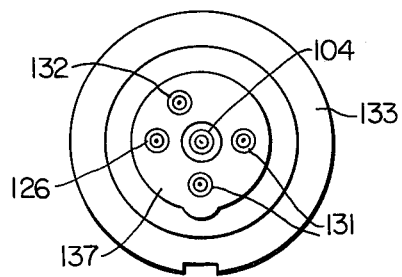
FIG. 5 is a plan view and
FIG. 6 is a perspective view of a third embodiment.
Figure 6:
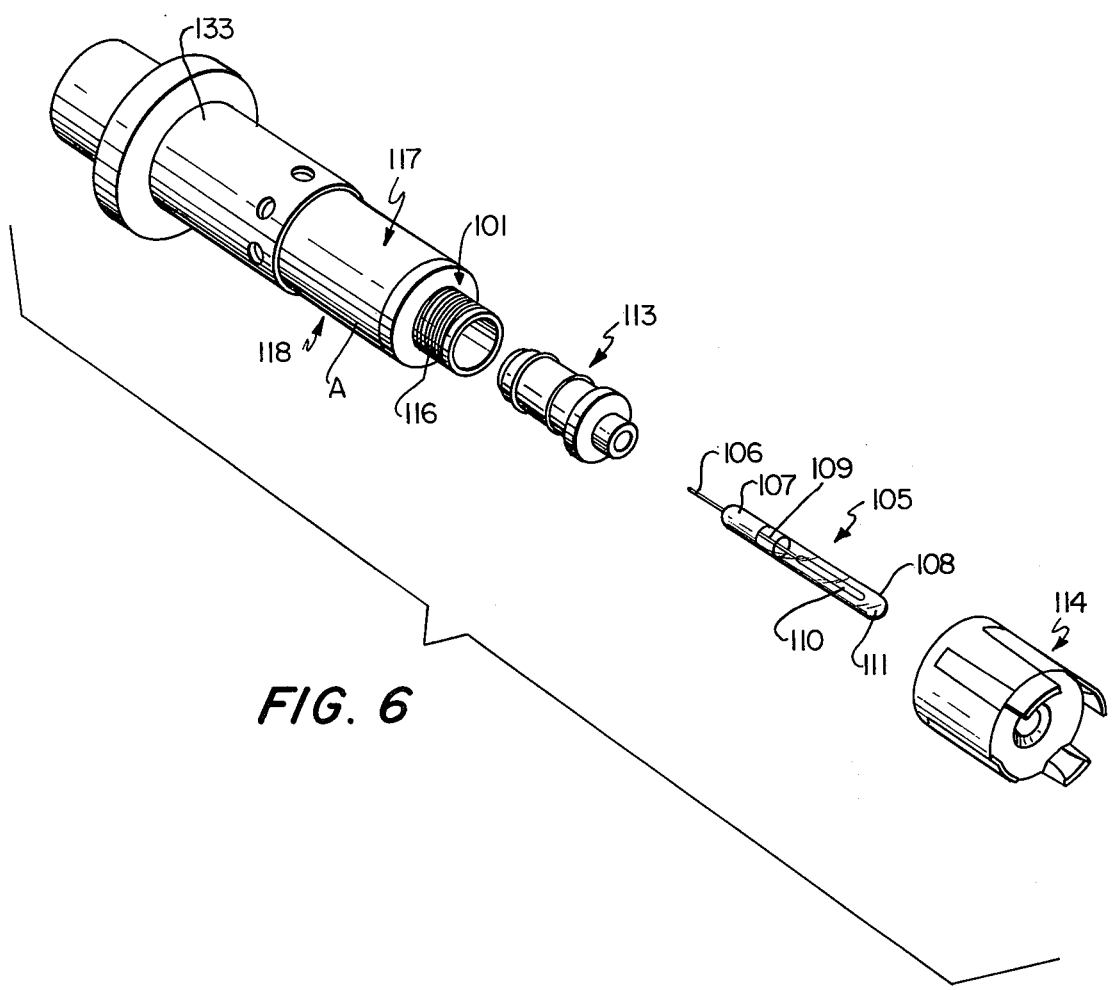

FIGS. 4 to 6 depict the third embodiment of the present invention, wherein the liquid junction of the present invention is employed in a so called combination pH electrode consisting of a reference electrode 118 and a glass electrode 105 combined together into one body.

In FIGS. 4, 5 and 6, 101 depicts a central body of cylindrical shape and 102 as a contact pin which can be easily inserted into the inside of the central body 101 or can be easily removed from it and is electrically connected with a detector (volt-meter) not shown in the figure, through a lead wire 103 and a lead pin 104; 105 is a glass electrode provided with necessary but minimum number of parts such as a cap member 107 which has a protruding lead pin 106, a glass membrane 108, an internal lead wire 109, an internal electrode 110 and an internal solution 111 (for example, a saturated aqueous solution of potassium chloride). The glass electrode 105 is constructed so as to be easily inserted into the inside of the central body 101 from its bottom and, of course, to be easily removed therefrom, if necessary, in order to make intimate contact between the said lead pin 106 and a concave portion 112 of the contact pin 102, inserting the lead pin 106 into the concave portion 112. 113 is a packing coated with the hydrophobic material polytetafluoroethylene resin and can be inserted easily into a clearance between the glass electrode 105 and the central body 101 to prevent the invasion of a sample solution into the inside of the central body 101 and of course, easily can be taken out. 114 is a protective cap of plastic material for the protection of the glass electrode and is fitted to the outside of the said glass electrode 105 using a screw 115 threaded on the inside of the cap and a screw 116 threaded on the lower end of the central body 101 and, of course, the protective cap can be easily fitted or taken off. The glass electrode 105 is fixed in the combination electrode by the central body 101, the packing 113 and the cap 114. 117 is a side wall prepared with the strong and hydrophobic plastic material polytetrafluoroethylene. The side wall 117 forms a liquid junction for reference electrode 118, and only on the surface of the side wall 117, the hydrophilic layer A is formed. Furthermore, the side wall 117 is fitted to the central body 101, using a screw 119 and a screw 121 threaded on the central body 101 and, of course, this can be fitted or taken off easily. 123 is an internal solution (for example, a saturated a saturated aqueous solution of potassium chloride) of the reference electrode and 124 is an internal electrode wherein the internal electrode is connected with a lead pin 126 through a lead wire 125. 127 is a second body which can be fitted or taken off easily using a screw thread 128 and a screw thread 129 attached to the inside wall of the upper part of the said side wall 117. 130 is a thermistor provided in the said second body 127 and is used for calibration of temperature. 131 is a lead pin connected to thermistor 130, 132 is a lead pin for connection to a ground and 133 is a metallic cap which can be easily fitted to the side wall 117 and to the second body 127 and, of course, easily taken off from them, using a screw 134 threaded at the inside wall of the cap, a screw 135 threaded at the outside wall of the side wall 117 and a screw 136 threaded at the outside wall of the second body 127.

For additional feeding of the internal solution 123, the metallic cap 133 and the second body 127 are removed.

As shown in FIG. 4, the combination electrode of the present invention is protected in the upper part by the said metallic cap 133, in the middle part by the said side wall 117 and in the lower part by the said protection cap 114, respectively. Further, in those drawings, 137 is a pin housing and 138, 139, 140 and 141 are O-rings.

The liquid junction obtained by the present invention is constructed as described above. Thus, since the surface of the liquid junction has a sufficient hydrophilic property, the liquid-liquid potential difference at the boundary surface between the surface of the liquid junction and the solution to be measured is much decreased and stabilized. Moreover, since the existence of the hydrophilic property is limited to only the surface area of the liquid junction and the hydrophobic property at the inner part of the liquid junction is retained unchanged, the leakage of internal liquid can also be kept very low.

By the combined effect of both characteristic properties, it becomes possible to determine an ionic concentration at a much superior accuracy to that which can be achieved by using any other conventional liquid junction.

We claim:

1. In a reference electrode comprising an internal electrode, an internal liquid and a liquid junction structure for separating said internal liquid from a liquid sample to be measured, the improvement wherein said junction structure comprises polytetrafluoroethylene having a hydrophillic layer on the liquid junction surfaces thereof.

2. A reference electrode according to claim 7 wherein the liquid junction is disposed at the base of said electrode.

3. A reference electrode according to claim 7 wherein the liquid junction is disposed at the side wall of said electrode.

4. A reference electrode according to claim 7 wherein the hydrophylic layer is formed by the reaction of sodium on polytetrafluoroethylene.

5. A reference electrode according to claim 4 wherein said reaction is performed in an organic solvent comprising naphthalene.

* * * * *

UNITED STATES PATENT AND TRADEMARK OFFICE
CERTIFICATE OF CORRECTION

PATENT NO. : 4,053,382
DATED : October 11, 1977
INVENTOR(S) : Hiroshi Maruyama and Masashi Watanabe It is certified that error appears in the above-identified patent and that said Letters Patent are hereby corrected as shown below:

Column 4, lines 26, 29 and 32, change "7" to -- 1 --.

Signed and Sealed this

Fourteenth Day of March 1978

[SEAL]

Attest:

RUTH C. MASON
*Attesting Officer*

LUTRELLE F. PARKER
*Acting Commissioner of Patents and Trademarks*